United States Patent
Shen

(10) Patent No.: US 10,231,850 B2
(45) Date of Patent: Mar. 19, 2019

(54) PROSTHETIC KNEE JOINT LOCKABLE INTO AN EXTENSION POSITION

(75) Inventor: Hsin Fa Shen, Taipei (TW)

(73) Assignee: PRO LIMB INTERNATIONAL CORP., New Taipei (TW)

( * ) Notice: Subject to any disclaimer, the term of this patent is extended or adjusted under 35 U.S.C. 154(b) by 1258 days.

(21) Appl. No.: 11/597,023

(22) PCT Filed: May 17, 2005

(86) PCT No.: PCT/DE2005/000894
§ 371 (c)(1),
(2), (4) Date: Mar. 7, 2008

(87) PCT Pub. No.: WO2005/112837
PCT Pub. Date: Dec. 1, 2005

(65) Prior Publication Data
US 2008/0281427 A1 Nov. 13, 2008

(30) Foreign Application Priority Data
May 19, 2004 (DE) .................... 20 2004 008 157 U

(51) Int. Cl.
*A61F 2/64* (2006.01)
*A61F 2/68* (2006.01)
(Continued)

(52) U.S. Cl.
CPC ............... *A61F 2/64* (2013.01); *A61F 2/644* (2013.01); *A61F 2002/30365* (2013.01);
(Continued)

(58) Field of Classification Search
CPC .... A61F 2/68; A61F 2/64; A61F 2/646; A61F 2002/6854
(Continued)

(56) References Cited

U.S. PATENT DOCUMENTS 688,936 A * 12/1901 Devol ...................... A61F 2/60
623/44
2,336,881 A * 12/1943 Mortensen ...................... 623/41
(Continued)

FOREIGN PATENT DOCUMENTS

CN 1125976 A 7/1996
DE 342833 C 10/1921
(Continued)

OTHER PUBLICATIONS

International Search Report from International PCT Application No. PCT/US2015/016075, dated May 19, 2015.
(Continued)

*Primary Examiner* — Marcia L Watkins
(74) *Attorney, Agent, or Firm* — Workman Nydegger

(57) ABSTRACT

The invention relates to a prosthetic joint which can be used as an artificial knee. Said prosthetic joint consists of a knee upper part (1), a knee lower part (2) and a fixing element (8) connecting said two lower parts. The knee upper part is rotationally arranged about the rotational axis (4) of the fixing element and rotation occurs counter to the force of an elastic element (17) which is arranged in knee lower part. Detachable fixing means (7), which are used to fix at least one rotational position, are provided between the knee upper part and the fixing element.

5 Claims, 4 Drawing Sheets

(51) Int. Cl.
*A61F 2/74* (2006.01)
*A61F 2/30* (2006.01)
*A61F 2/50* (2006.01)

(52) U.S. Cl.
CPC ............... *A61F 2002/30367* (2013.01); *A61F 2002/30405* (2013.01); *A61F 2002/30434* (2013.01); *A61F 2002/30507* (2013.01); *A61F 2002/503* (2013.01); *A61F 2002/5033* (2013.01); *A61F 2002/5073* (2013.01); *A61F 2002/6818* (2013.01); *A61F 2002/6854* (2013.01); *A61F 2002/74* (2013.01); *A61F 2220/0025* (2013.01); *A61F 2220/0033* (2013.01); *A61F 2220/0041* (2013.01)

(58) Field of Classification Search
USPC ............................. 623/32, 35, 38, 39, 41, 43
See application file for complete search history.

(56) References Cited

U.S. PATENT DOCUMENTS

| | | | |
|---|---|---|---|
| 2,561,370 A | | 7/1951 | Henschke et al. |
| 3,533,651 A | * | 10/1970 | Prahl .................. A61F 2/64 403/93 |
| 3,723,997 A | | 4/1973 | Kolman |
| 3,982,279 A | | 9/1976 | Valenti et al. |
| 4,152,787 A | | 5/1979 | Meggyesy |
| RE31,673 E | | 9/1984 | Blatchford et al. |
| 4,578,083 A | * | 3/1986 | Williams ................. 623/42 |
| 4,595,179 A | * | 6/1986 | Glabiszewski ............. 267/221 |
| 4,685,926 A | * | 8/1987 | Haupt .................. A61F 2/64 623/43 |
| 5,062,857 A | | 11/1991 | Berringer et al. |
| 5,704,945 A | * | 1/1998 | Wagner et al. ............ 623/44 |
| 5,746,774 A | | 5/1998 | Kramer et al. |
| 5,888,237 A | | 3/1999 | Shiraishi et al. |
| 5,895,430 A | * | 4/1999 | O'Connor ................ 623/39 |
| 5,899,943 A | | 5/1999 | Shiraishi et al. |
| 6,159,248 A | | 12/2000 | Gramnas |
| 6,206,933 B1 | | 3/2001 | Shorter et al. |
| 6,471,664 B1 | * | 10/2002 | Campbell et al. .......... 602/16 |
| 6,673,117 B1 | | 1/2004 | Soss et al. |
| 6,706,074 B1 | | 3/2004 | Chen |
| 7,544,215 B2 | | 6/2009 | Speckbacher et al. |
| RE42,903 E | | 11/2011 | Deffenbaugh et al. |
| 8,268,012 B1 | | 9/2012 | Cheng et al. |
| 9,770,346 B2 | | 9/2017 | Karlsson et al. |
| 9,770,347 B2 | | 9/2017 | Shen |
| 2003/0050712 A1 | | 3/2003 | Shen |
| 2006/0259153 A1 | | 11/2006 | Harn et al. |
| 2007/0173953 A1 | | 7/2007 | Imakita et al. |
| 2007/0208431 A1 | | 9/2007 | Bisinger et al. |
| 2008/0281427 A1 | | 11/2008 | Shen |
| 2010/0100197 A1 | | 4/2010 | Kremser et al. |
| 2011/0098828 A1 | | 4/2011 | Balboni et al. |
| 2011/0270415 A1 | | 11/2011 | Chen et al. |
| 2012/0150318 A1 | | 6/2012 | Chabloz |
| 2012/0310372 A1 | | 12/2012 | Omarsson et al. |
| 2013/0204395 A1 | | 8/2013 | Gramnaes |

FOREIGN PATENT DOCUMENTS

| | | |
|---|---|---|
| DE | 362891 C | 11/1922 |
| DE | 561844 C | 10/1932 |
| DE | 726228 C | 2/1943 |
| DE | 805768 C | 5/1951 |
| DE | 811254 C | 8/1951 |
| DE | 8417478 U1 | 6/1984 |
| DE | 20119049 U1 | 2/2002 |
| DE | 202005021906 U1 | 6/2011 |
| EP | 0095872 A | 5/1983 |
| EP | 0095872 A1 | 12/1983 |
| EP | 1166726 A1 | 6/2001 |
| EP | 1 166 726 A1 | 1/2002 |
| EP | 1 570 817 A1 | 9/2005 |
| EP | 2478875 A2 | 7/2012 |
| GB | 2270473 A | 3/1994 |
| GB | 2331462 A | 11/1997 |
| TW | 564742 U | 12/2003 |
| WO | WO 95/30391 | 5/1995 |
| WO | WO 03/092545 A2 | 5/2003 |
| WO | 2009066055 A2 | 5/2009 |

OTHER PUBLICATIONS

"Medic OFM2-HD Knee Available with 275 lb. Weight Limit", The O&P EDGE, Oandp.com, Dec. 2008, 3 Pages.

Medi OFM2 (and Medi OFM2 view 2). Youtube. Published Oct. 11, 2012.

\* cited by examiner

PROSTHETIC KNEE JOINT LOCKABLE INTO AN EXTENSION POSITION

BACKGROUND OF THE INVENTION

Field of the Invention

The present invention relates to a prosthetic joint having an upper part, a lower part, and a clamping connecting the two parts.

Description of Related Art

A prosthetic joint for use as an artificial knee, consisting of an upper part, a lower part and a clamping member connecting said two parts, said upper part of the knee being disposed for rotation about an axis of rotation of the clamping member and the rotation occurring against the force of an elastic element disposed in the lower part of the knee, is known from EP 1 166 726 A1 or DE 201 19 049 U1 for example. This mechanism allows for braking flexion whilst extension is allowed to occur without much braking.

SUMMARY OF THE INVENTION

It is the object of the present invention to improve such a prosthetic joint in such a manner that it may be fixed at little expense in certain positions, so for example in the extended position. This is of great advantage to fresh amputees that are not yet very skilled in controlling a knee joint. Hitherto, in practice, two different knee joints have been used one after the other, i.e., the prostheses needed to be modified. Both the use of two knee joints and the modification were cost prohibitive so that there was a desire to combine both functions in one knee joint.

In accordance with the invention, there is provided a prosthetic joint for use as an artificial knee, consisting of an upper part, a lower part and a clamping member connecting said two parts, said upper part of the knee being disposed for rotation about an axis of rotation of the clamping member and the rotation occurring against the force of an elastic element disposed in the lower part of the knee, characterized in that releasable fixing means for fixing at least one position of rotation are provided between the upper part of the knee and the clamping member.

According to a preferred embodiment of the invention, the fixing means is a pawl hinged to the upper part of the knee, said pawl being engageable into a recess of the clamping member. In the alternative, solutions using clamping levers, screws, detent means or the like may be used. In the embodiment shown, the pawl has means for fixing its position on the upper part of the knee. Advantageously, the pawl is biased in a locking position by an elastic element, e.g., a spring. The pawl preferably has an actuation lever. The fixable position of rotation is for example the extension position.

According to the preferred embodiment of the invention, the axis of rotation of the clamping member is eccentrically connected for rotation to at least one advance push-rod that is hinged to a spring piston of a spring carried in the lower part of the knee. The spring preferably is a mechanical compression spring, its spring path and characteristic being adjustable by a screwing device.

Between the clamping member and the lower part of the knee there is preferably provided an adjustable adjusting wedge.

BRIEF DESCRIPTION OF THE DRAWINGS

The invention will be understood better upon reading the exemplary description accompanying the drawing.

DETAILED DESCRIPTION OF THE INVENTION

Figure 1:
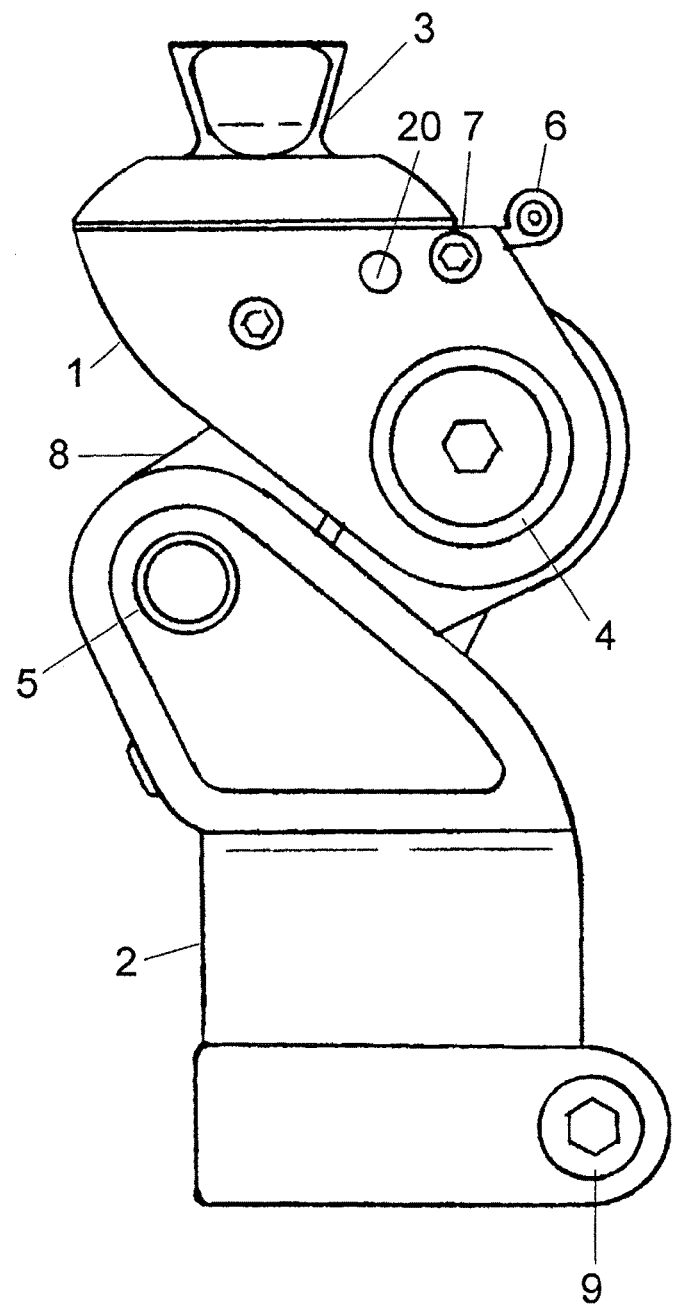
FIG. 1 is a side view of a prosthetic joint in the extension position.
Figure 2:
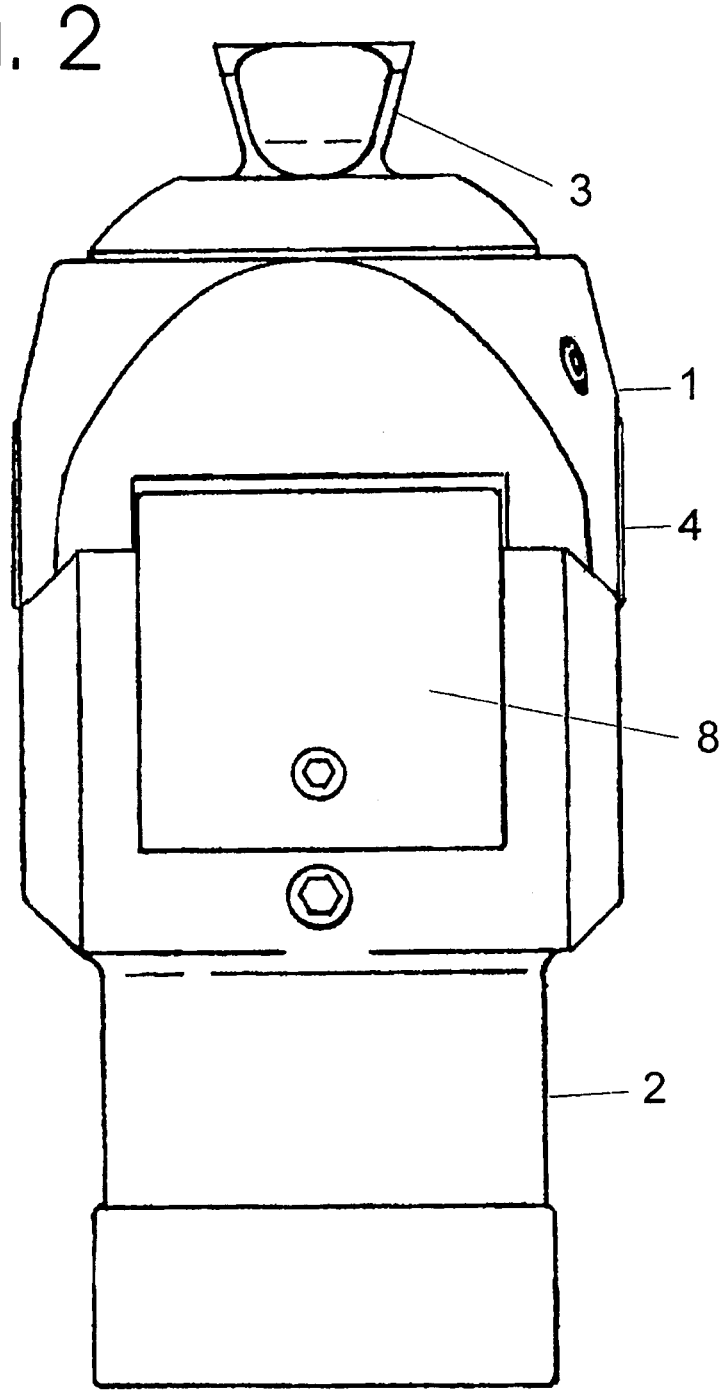
FIG. 2 is a back view of the prosthetic joint of FIG. 1.
Figure 3:
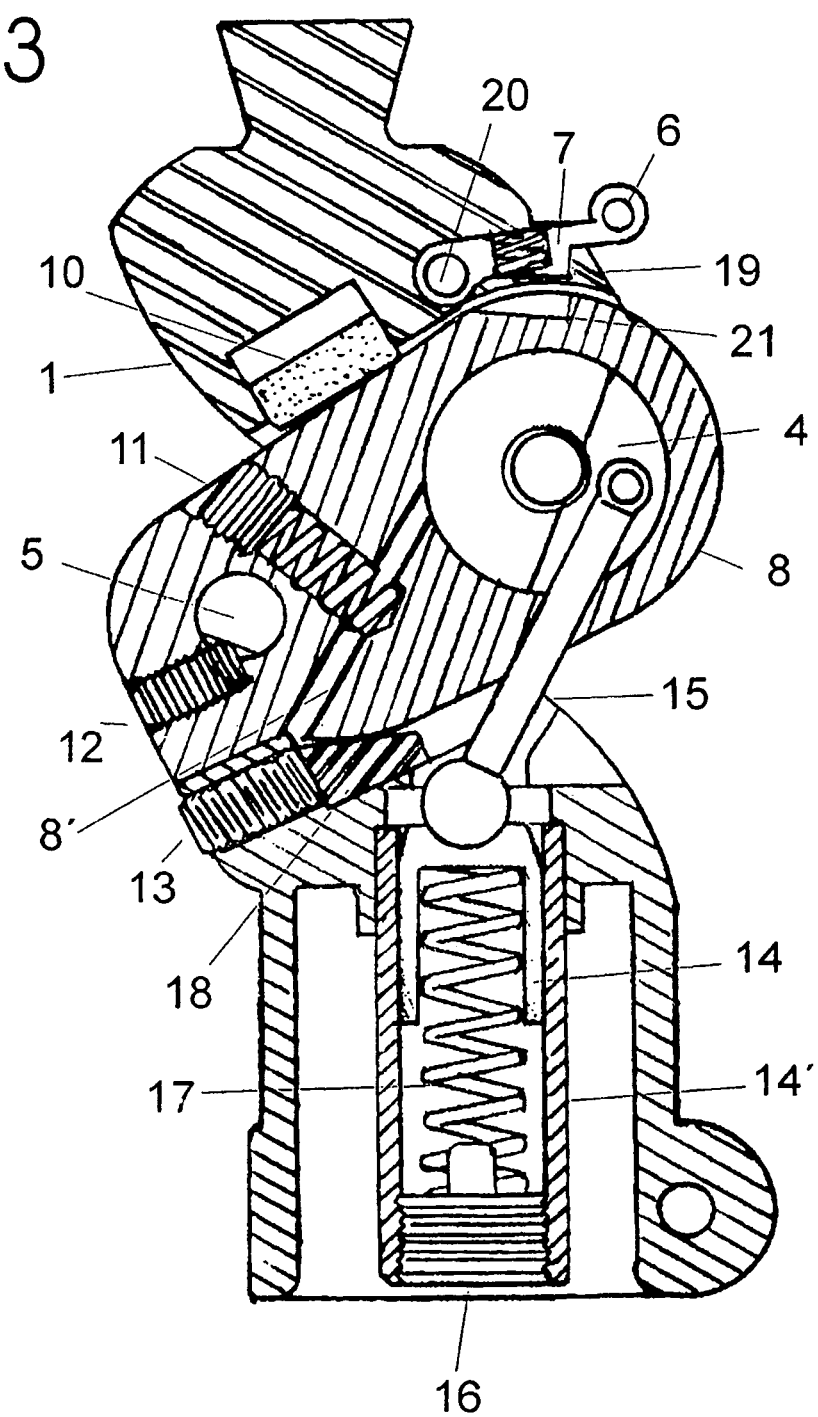
FIG. 3 is a partial sectional view in elevation of the prosthetic joint of FIG. 1.
Figure 4:
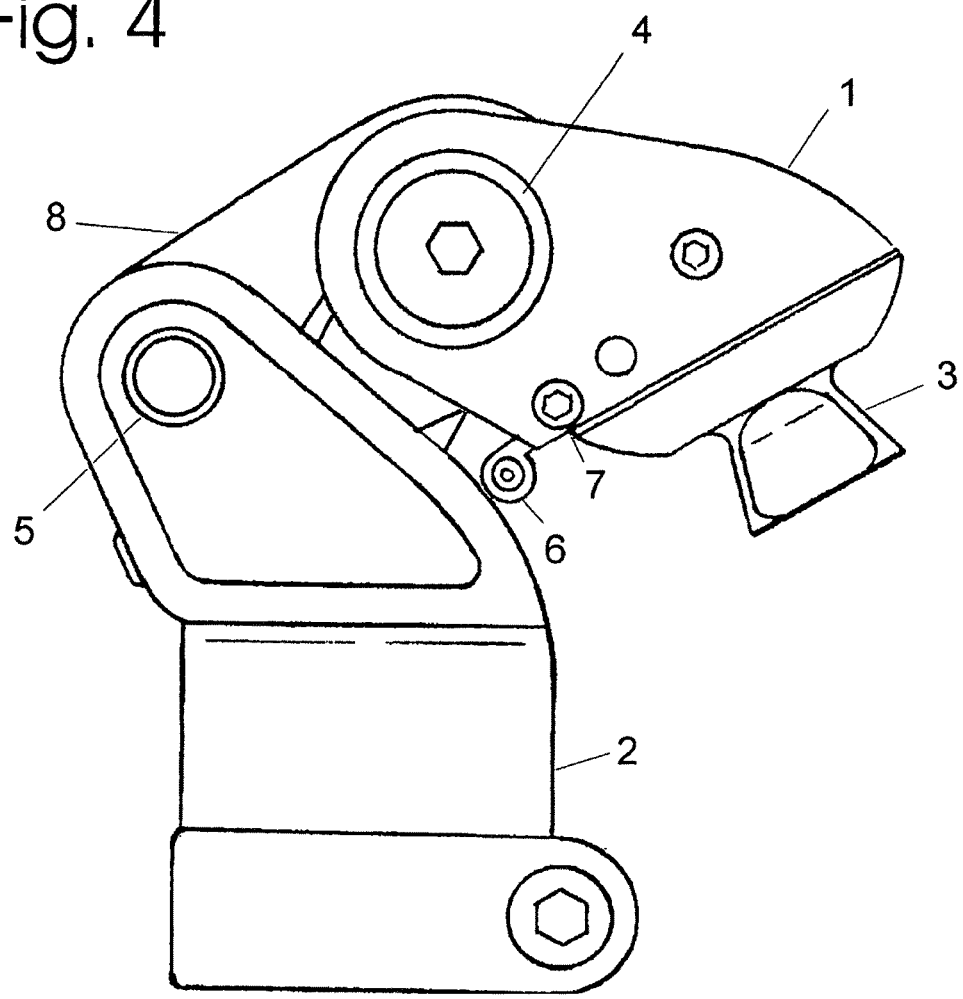
FIG. 4 shows the prosthetic joint of FIG. 1 in the flexion position.

The FIGS. 1, 2 and 3 show the prosthetic joint from the outside. It consists of an upper part 1, a lower part 2 and a clamping member 8 connecting said two parts together. At its top end, the upper part 1 of the knee is provided in a known manner with a pyramid 3 for connection to a prosthetic shank (not shown). At its bottom end, the lower part 2 of the knee has a bracket with a clamping screw 9 for connection to a prosthetic tube (not shown). The clamping member 8 is carried on a brake hinge axis 5, between two legs of the lower part 2 of the knee. The upper part 1 of the knee is carried on an axis of rotation 4 of the clamping member 8 and is pivotal between the extension position (FIG. 1) and the flexion position (FIG. 4).

The functioning of the prosthetic joint will now be explained referring to FIG. 3. The clamping member 8 is configured to have a slot 8' and the upper part is configured to selectively rotate relative to the clamping member about the axis of rotation 4 that is non-rotatably retained in the lateral legs of the upper part 1 of the knee. In the extension position, the weight of the user pushes onto the upper part 1 of the knee and against an extension limit stop 10 retained in a recess that is open toward the top of the clamping member 8. The exerted force acts to close the slot 8' for the clamping member 8 to close harder about the axis of rotation 4 and to clampingly engage therewith. To adjust the clamping effect, the threshold of the charge and the progression of the braking effect, there are provided in a known manner a brake regulation screw 11 with spring, a fixing screw 12 for the hinge axis 5 and a wedge 18 that is adjustable by means of another screw 13. Between the axis of rotation 4 and a damping arrangement disposed in the lower part of the knee and consisting of a piston 14', a cylinder 14, a spiral spring 17 biasing said cylinder and an adjusting screw 16, there is disposed an advance push-rod 15. At its lower end, the advance push-rod 15 is connected to the cylinder 14 and is eccentrically hinged to the axis of rotation 4 at its upper end. If the prosthetic joint is brought from the extension position (FIGS. 1, 2 and 3) to the flexion position (FIG. 4) (when the knee is being bent), the clamping effect of the clamping member 8 is cancelled and the upper part 1 of the knee rotates clockwise about the axis of rotation 4. This occurs against the force of the spring 17 of the damping arrangement that is compressed by the advance push-rod. If the prosthetic joint is returned to the flexion position, the damping arrangement acts as an advancing mechanism and the advance push-rod 15 pushes the axis of rotation 4 with the upper part 1 of the knee back into the flexion position.

If the prosthetic joint is to be used as a "first" prosthesis after amputation, the upper part 1 of the knee can be fixed with respect to the clamping member 8 by a stopper device. Said stopper device consists of a pawl 7 that is carried above the clamping member 8 on the upper part 1 of the knee so as to be pivotal about a pin 20. In the extension position, said pawl 7 can be engaged into a recess 21 of the clamping member 8 so as to stop the movement of the upper part 1 of the knee. The pawl 7 has an actuation lever 6 guided outward and is biased in the stop position by a spring 19. A locking device for fixing the pawl in the engaged or disengaged position is provided.

The invention claimed is:

1. A prosthetic joint for use as an artificial knee, comprising:
    an upper part comprising first and second upper legs,
    a lower part comprising first and second lower legs,
    a clamping member connecting said upper and lower parts, the clamping member being coupled to the upper part via a first member having a circular cross section disposed between the first and second upper legs and defining a first rotation axis for relative rotation between the clamping member and the upper part, and coupled to the lower part via a second member having a circular cross section disposed between the first and second lower legs and defining a second rotation axis for relative rotation between the clamping member and the lower part, wherein a clockwise rotation of the upper part about the first rotation axis occurs against a force of a first elastic element disposed in the lower part of the knee by connection of the first member to the first elastic element via an advance push rod,
    a slot defined in the clamping member and configured so that a force exerted by a weight of a user on the upper part acts to close the slot for the clamping member to clampingly engage with the first member and restrict relative rotation between the upper part and the clamping member, and
    a pawl separate from the slot and provided between the upper part of the knee and the clamping member, the pawl having an actuation lever and being hinged to the upper part of the knee, the pawl being carried above the clamping member and selectively engageable into a recess of the clamping member to stop and fix movement of the upper part of the knee relative to the clamping member and the pawl being biased in a locking position by a second elastic element, whereby the prosthetic joint can be fixed completely in an extension position with the pawl by an amputee for beginner training such that rotation of the lower part relative to the upper part is prevented when the pawl is engaged in the recess of the clamping member in the locking position.

2. The prosthetic joint as set forth in claim 1, characterized in that an adjustable wedge is provided between the clamping member and the lower part of the knee.

3. The prosthetic joint as set forth in claim 1, wherein the lower part comprises a cylinder and the first elastic element.

4. A prosthetic joint for use as an artificial knee, comprising:
    an upper part comprising first and second upper legs,
    a lower part comprising first and second lower legs,
    a clamping member connecting said upper and lower parts, the clamping member being coupled to the upper part via a first member having a circular cross section disposed between the first and second upper legs and defining a first rotation axis for relative rotation between the clamping member and the upper part, and coupled to the lower part via a second member having a circular cross section disposed between the first and second lower legs and defining a second rotation axis for relative rotation between the clamping member and the lower part, wherein a clockwise rotation of the upper part about the first rotation axis occurs against a force of a first elastic element disposed in the lower part of the knee,
    a slot defined in the clamping member and configured so that a force exerted by a weight of a user on the upper part acts to close the slot for the clamping member to clampingly engage with the first member and restrict relative rotation between the upper part and the clamping member, and
    a pawl separate from the slot and provided between the upper part of the knee and the clamping member, the pawl having an actuation lever and being hinged to the upper part of the knee, the pawl being carried above the clamping member and selectively engageable into a recess of the clamping member to stop and fix movement of the upper part of the knee relative to the clamping member and the pawl being biased in a locking position by a second elastic element, whereby the prosthetic joint can be fixed completely in an extension position with the pawl by an amputee for beginner training such that rotation of the lower part relative to the upper part is prevented when the pawl is engaged in the recess of the clamping member in the locking position; and
    an advance push-rod with a first end that is eccentrically connected for rotation with respect to the clamping member by connection to the first member, the advance push rod having a second end being hinged to a spring piston of the first elastic element carried in the lower part of the knee.

5. The prosthetic joint as set forth in claim 4, characterized in further comprising a screw configured to adjust a length of the first elastic element.

* * * * *